United States Patent
Stanton et al.

(10) Patent No.: US 9,625,286 B2
(45) Date of Patent: Apr. 18, 2017

(54) ADJUSTABLE PROBE HOLDER ASSEMBLY FOR AN INSPECTION SENSOR

(71) Applicants: Matthew Edward Stanton, Reading, MA (US); Ernest Bill, East Bridgewater, MA (US)

(72) Inventors: Matthew Edward Stanton, Reading, MA (US); Ernest Bill, East Bridgewater, MA (US)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 134 days.

(21) Appl. No.: 14/593,699

(22) Filed: Jan. 9, 2015

(65) Prior Publication Data

US 2016/0202093 A1   Jul. 14, 2016

(51) Int. Cl.
*G01N 29/24*   (2006.01)
*G01D 11/30*   (2006.01)
*G01N 29/22*   (2006.01)

(52) U.S. Cl.
CPC ........... *G01D 11/30* (2013.01); *G01N 29/225* (2013.01)

(58) Field of Classification Search
CPC .... G21C 17/002; G21C 17/003; G21C 17/01; G21C 17/013; G21C 17/06; G21C 17/07; G01N 29/222; G01N 29/225; G01N 29/226; G01N 29/227; G01N 2291/2634; G01N 2291/2636; G01D 11/30
USPC .................... 376/252, 249, 250; 73/633, 634
See application file for complete search history.

(56) References Cited

U.S. PATENT DOCUMENTS

| | | | | |
|---|---|---|---|---|
| 4,139,822 | A * | 2/1979 | Urich | G01N 27/9033 324/219 |
| 8,109,160 | B2 * | 2/2012 | Bossi | G01N 29/225 73/584 |
| 8,621,946 | B1 * | 1/2014 | Nefos | A61B 8/12 600/437 |
| 9,316,512 | B2 * | 4/2016 | Georgeson | G01D 11/30 |
| 2009/0079821 | A1 * | 3/2009 | Bousquet | A61B 1/0055 348/65 |
| 2009/0278924 | A1 * | 11/2009 | Heyworth | F01D 21/003 348/82 |
| 2011/0018530 | A1 * | 1/2011 | Bousquet | G01N 27/9033 324/240 |

(Continued)

*Primary Examiner* — Peter MacChiarolo
*Assistant Examiner* — Natalie Huls
(74) *Attorney, Agent, or Firm* — C. Tricia Liu (57) ABSTRACT

An adjustable probe holder assembly is disclosed for an inspection or measurement sensor, such as an ultrasound transducer, eddy current sensor, magnetic thickness sensor or optical image sensor, in order to position the sensor in a confined space using an extended arm with an adjustable curvature. The probe holder has at least two elongated holding arms, among which a first arm and a second arm, each having a probe end and a holding end, wherein the probe end of each of the holding arms are attached to the probe and the at least two arms remain substantially parallel and very close to each other when the probe holder is at a non-operational status. The two arms bulge open away from each other due to either a tension force or a compression force being exerted along the longitudinal direction of either one of the arms, holding the probe to be against the test surface of the test object.

23 Claims, 11 Drawing Sheets

(56) References Cited

U.S. PATENT DOCUMENTS

| | | | |
|---|---|---|---|
| 2011/0260721 A1* | 10/2011 | Fischer | G01B 7/105 324/229 |
| 2012/0291583 A1* | 11/2012 | Bousquet | F01D 21/003 74/490.04 |
| 2013/0310650 A1 | 11/2013 | Hales | |
| 2014/0318257 A1* | 10/2014 | Udell | G01N 29/265 73/633 |
| 2015/0374331 A1* | 12/2015 | Cho | A61B 8/4444 600/462 |

* cited by examiner

ADJUSTABLE PROBE HOLDER ASSEMBLY FOR AN INSPECTION SENSOR

FIELD OF THE INVENTION

The present invention pertains to measuring devices for performing nondestructive testing (NDT) and, more particularly, to NDT inspection probes with extension wands for positioning a sensing device on an inspection surface where access to the surface is obstructed.

BACKGROUND OF THE INVENTION

Nondestructive testing probes are used for measuring thickness, or inspecting for flaws in critical portions of various objects, such as pipes, bridges, aircraft, castings, and turbine blades. Access to a portion of an object to be inspected may be limited by the shape of the object, or by its location relative to other objects.

Handles and wands for proper positioning of sensors on an inspection surface are known in existing practice. For instance, insertion wands for boiler tube wall inspection are known to incorporate a sensor that is attached to a semi flexible, thermoplastic tube capable of concentrically following the inside diameter of the tube. A semi flexible, plastic tube wand may not be well suited for positioning a sensor on an inspection surface that is not in a tubular test object. In non-tubular test objects, the inner surface of the object may not guide the probe to the surface, and the shape of the wand may not conform to the surface.

Other examples of probe positioning devices are straight or bent angle extension wands with a fixed angle between a sensor and a wand end. The arms of such wands are typically straight, or bent rigid tubes or rods. Still other probe positioning devices are straight or bent angle wands with a pivot yoke holding a sensor at the distal end, allowing angular movement of the sensor around the pivot axis. Straight wands are useful where it is possible to have line of sight access to the inspection surface of a test object. Straight wands are not suitable for inspecting test objects with inspection surfaces behind a bend in the object, or behind another immovable object. Bent angle wands have one or more bends at fixed distances from the handle, allowing the sensor to be placed on an inspection surface behind a bend in a test object or behind an immovable object. The angles and positions of a bent wand are designed to accommodate bends of known angles at known distances from the inspection access position, to the inspection surface on the test object. A wand designed for inspection of surfaces at certain angles and distance from an access position may not be suitable for inspecting another surface at other angles or distances. In instances such as a test surface around a bend at the end of a long straight crevice, neither a bent or straight wand will enable inspection. Where bent or straight wands are suitable, several different wands may be needed to inspect surfaces in different locations of one or more test objects. Additional wands are costly and may result in additional expenses for transportation, training, and sensor calibration.

US Pat. No. 2013/0310650 discloses a laryngoscope with a thumb-operable guided tube and an adjustable curving mechanism, which can be inserted into and released from the airway of a patient. Although this mechanism is not in the spirit of non-destructive inspection, it does place an articulating probe in a confined and obstructed space for the purpose for inspection. However the range of the obstructed space is limited to range of shape of anatomical features thereby limiting the required range and size of the device. The operation of the mechanism requires tendons retracting within rigid blades each having a fixed volume. The range of articulation is to an extent determined by the length of the tendons and blades and the dimension of the blades in the plane of articulation. The blade thickness in the plane of articulation limits the minimum thickness of the device and may prohibit inspection in confined spaces.

Available devices do not fully meet the need to accurately position sensors on a variety of obstructed surfaces of test objects, in a timely and cost effective manner. Some test objects may require equipment disassembly and reassembly to allow inspection when an appropriate wand is not available. Skilled mechanics, special tools, oil, gaskets and spare parts may be needed adding further expense and delay to an inspection. A further risk of disassembly is the possibility of incidental damage or misassembly. Furthermore, disassembly is not possible for some test objects such as cast turbine blades. It would be advantageous to inspect objects with minimal disassembly, or when inspection is not possible by other means.

SUMMARY OF THE INVENTION

Accordingly, it is an object of the present disclosure to include a means of adjustably holding two or more arms of an inspection device with eccentrically opposed stresses on the arms (one arm adjustable, another arm fixed), so as to cause the arms to bend. The bending deflects an inspection sensor housed inside a probe in an adjustable arc in the direction of the arm under tension. Reversing the direction of forces applied to the arm ends reverses the curvature of the arms.

It is further an object of the present disclosure to provide a probe holder assembly that embodies two or more bendable, strip-shaped arms working together to adjust the arm curvature, and that enables inspection of a test object in a remote, obstructed, or confined space. The strip-shaped arms generally extend lengthwise, the broad sides of which are each clamped, or joined together at (or near at) the housing holding the inspection sensor in an overlapping manner, and are adjusted at the broad ends of the strips away from the sensor housing.

It is further an object of the present disclosure to have an embodiment of the probe holder assembly include a means of electronically connecting the sensor to a measurement instrument.

It is further an object of the present disclosure to have an embodiment of the probe holder assembly include a re-attachable sensor housing that can be attached at a fixed angle, or at a variable angle with an incorporated pivot joint, to a probe coupling. The probe coupling itself can be an integral part of the probe holder assembly or re-attachable as well.

It is yet further an object of the present disclosure to have the arm curvature shaped with one or more collars that restrict the lengthwise separation of the arms, which are not otherwise constrained by attachments to the housing, holders, or other arms.

It is yet further an object of the present disclosure to have more than one adjustable arm affect the curvature of the positioning arms.

It is yet further an object of the present disclosure to have opposite ends of a single arm in a loop affect the arm curvature.

Many advantages of the positioning device built according to the teachings herein disclosed may be appreciated by those skilled in the art. The first is the use of thin arms in a probe holder assembly capable of passing through narrow openings, and transmitting forces applied at a near end to a far end causing a bending moment and curvature in the short, broad side of the arms for controlled positioning of a measurement sensor. A second use of the probe holder assembly permits active pivoting of the probe housing containing a measurement sensor at the sensor end of the variably curved arms.

DETAILED DESCRIPTION OF THE INVENTION

Table 1 is purposed for assisting the reading of the present disclosure, and should not be construed as a limitation of the scope of the present disclosure.

TABLE 1

Components of the present disclosure

| Numeral in figures | On Figure | Associated component |
|---|---|---|
| 1a | 1, 1a, 1b, 5, 5a, 5b, 5c, 5d, 5e, 8, 9 | a-type probe |
| 1b | 2 | b-type probe (with electrical connection) |
| 1c | 3 | c-type probe (re-attachable) |
| 1d | 3a | d-type probe (re-attachable with electrical connection) |
| 1e | 3b, 3c | e-type probe (tilting) |
| 1f | 4, 4a, 4b | f-type probe (tilting with pivots) |
| 2 | 1, 1a, 1b, 2, 3, 3a, 3b, 3c, 4, 4a, 4b, 5, 5a, 5b, 5c, 5d, 5e, 8 | Fixed arm |
| 3 | 1, 1a 1b, 2, 3, 3a, 3b, 3c, 4, 4a, 4b, 5, 5a, 5b, 5c, 5d, 5e, 8 | Adjusting arm |
| 3a | 8 | Second adjusting arm |
| 4 | 1, 1a, 1b, 3 | Handle |
| 4a | 2, 3a | Cabled handle |
| 4b | 5e | Movable sleeve handle |

TABLE 1-continued

Components of the present disclosure

| Numeral in figures | On Figure | Associated component |
|---|---|---|
| 4c | 8 | Multiple arm handle |
| 5a | 1, 1a, 1b | Adjusting actuator screw |
| 5b | 1, 1a, 1b | Adjusting actuator retainer |
| 5a1 | 8 | First adjusting actuator screw |
| 5b1 | 8 | First adjusting actuator retainer |
| 5a2 | 8 | Second adjusting actuator screw |
| 5b2 | 8 | Second adjusting actuator retainer |
| 5c | 1, 1a 1b, 2, 3, 3a, 5, 5a, 5b, 5c, 5d, 5e | Adjusting actuator |
| 5d | 8 | First adjusting actuator |
| 5e | 8 | Second adjusting actuator |
| 6 | 1, 1a 1b, 3 | Direct cable |
| 6a | 2, 3a | Instrument cable |
| 6b | 2, 3a | Probe cable |
| 7 | 1, 1a, 1b, 2 | Measuring instrument |
| 8 | 1, 1a, 1b | Measuring target |
| 9 | 3, 4, 4a, 4b | Joint |
| 9a | 3a | Cable joint |
| 9b | 3b, 3c | Pivoting joint |
| 10 | 3, 3b, 3c, 4, 4a, 4b | Coupling |
| 10a | 3a | Cable-hosting coupling |
| 11 | 5a, 5b | Collar |
| 11a1 | 5c | Multiple collar |
| 11a2 | 5c | Multiple collar |
| 11b | 5d | Joined collar |
| 11c | 5e | Movable sleeve |
| 12 | 5e | Movable sleeve adjusting handle |
| 12a | 5e | Movable sleeve adjusting knob |
| 12b | 5e | Movable sleeve adjusting knob guide |
| 16a1 | 6 | Tapered adjusting arm (lateral view) |
| 16at | 6 | Tapered adjusting arm (vertical view) |
| 16b | 6 | Narrow-waist adjusting arm (vertical view) |
| 16c | 6 | Hollow point adjusting arm (lateral view) |
| 16l | 6 | Rectangular adjusting arm (lateral view) |
| 16t | 6 | Rectangular adjusting arm (vertical view) |
| 17 | 7 | Thick width arm |
| 17a | 7 | Thin width arm |
| 18 | 8 | Arm attachment |
| 19 | 9 | Adjustable arm loop |
| 19a | 9 | First loop arm |
| 19b | 9 | Second loop arm |
| 20 | 4, 4a, 4b | First pivot link |
| 21 | 4, 4a, 4b | Second pivot link |

It should be understood that various changes may be made and equivalents may be substituted for elements thereof without departing from the spirit and scope of the invention. The embodiment described herein and the claims described hereof are not to be read restrictively, unless there is clear and convincing evidence manifesting a certain exclusion, restriction, or disclaimer.

Figure 1:
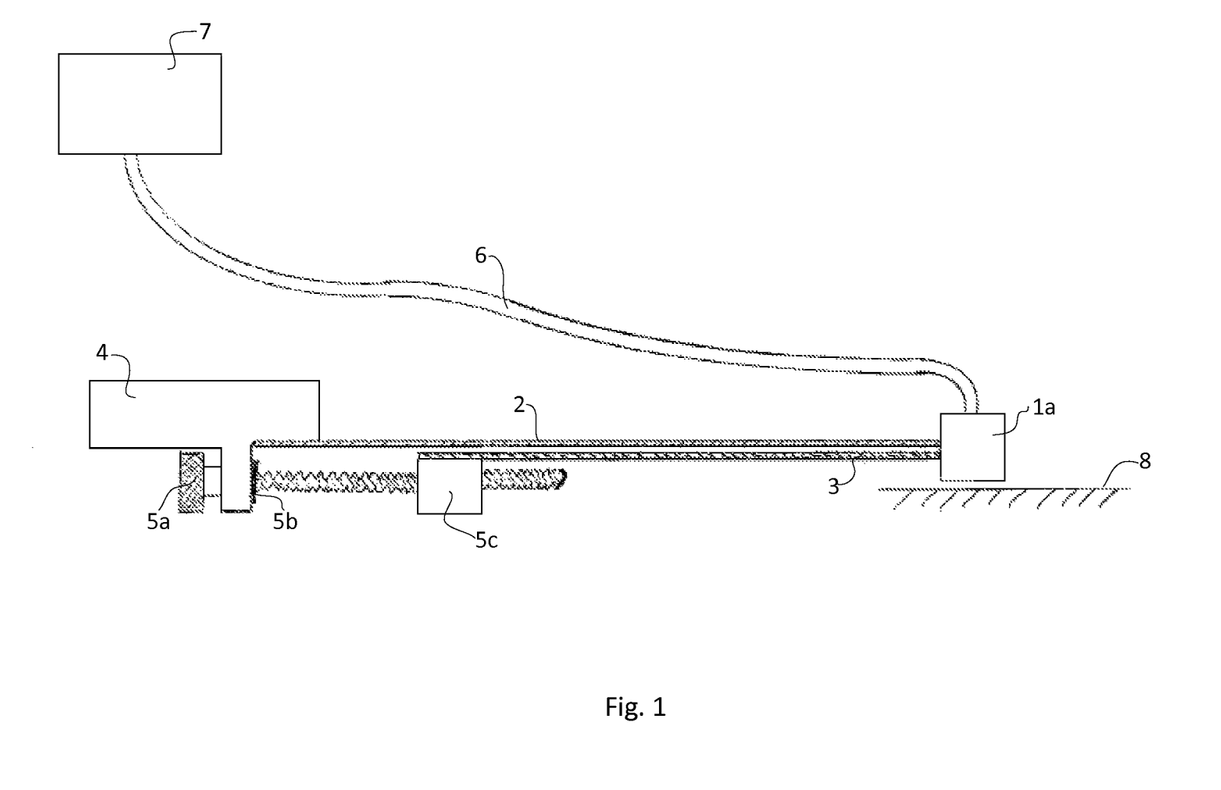
FIG. 1 is a profile view of an embodiment of a probe holder assembly with the arms in straight position.

Referring to FIG. 1, the preferred embodiment of the probe holder assembly of the present disclosure is comprised of an a-type probe 1a housing a sensor (not shown), a fixed arm 2, an adjusting arm 3, a handle 4, an adjusting actuator screw 5a, an adjusting actuator retainer 5b, an adjusting actuator 5c, a direct cable 6, a measuring instrument 7, and a measuring target 8.

The probe holder assembly is configured to be able to alter the angle of a-type probe 1a (connected to measuring instrument 7 by means of direct cable 6) so that it can adjust to bends and obstructions around measuring target 8. Handle 4 holds fixed arm 2 that is connected to a-type probe 1a as well as adjusting actuator screw 5a and adjusting actuator retainer 5b. Adjusting actuator 5c is connected to adjusting actuator screw 5a and adjusting actuator retainer 5b, as well as adjusting arm 3. Adjusting arm 3 is connected to a-type probe 1a. The user turns adjusting actuator screw 5a clockwise and counterclockwise, which when constrained by adjusting actuator retainer 5b, extends and retracts adjusting actuator 5c so that adjusting arm 3 bends, and tilts the angle of a-type probe 1a. Alternate adjusting positions of the probe holder assembly examining alternate positions of measuring target 8 are shown in FIGS. 1a and 1b.

Figure 1A:
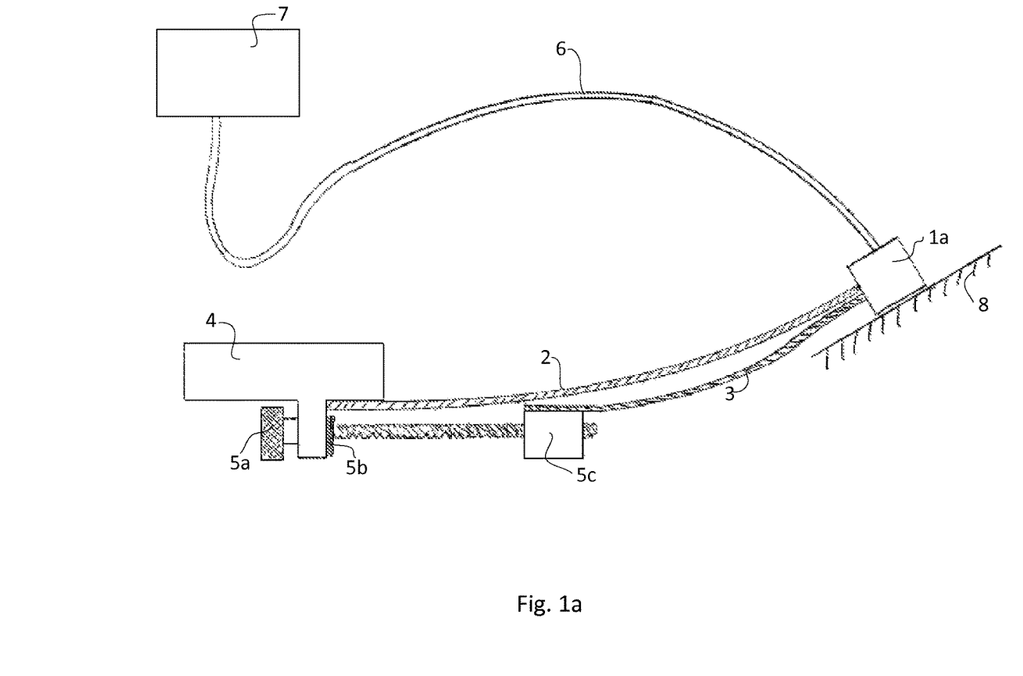
FIG. 1a is a view of the probe holder assembly shown in FIG. 1 with the adjustment arm extended and curved in an arc shape in a first direction.
Figure 1B:
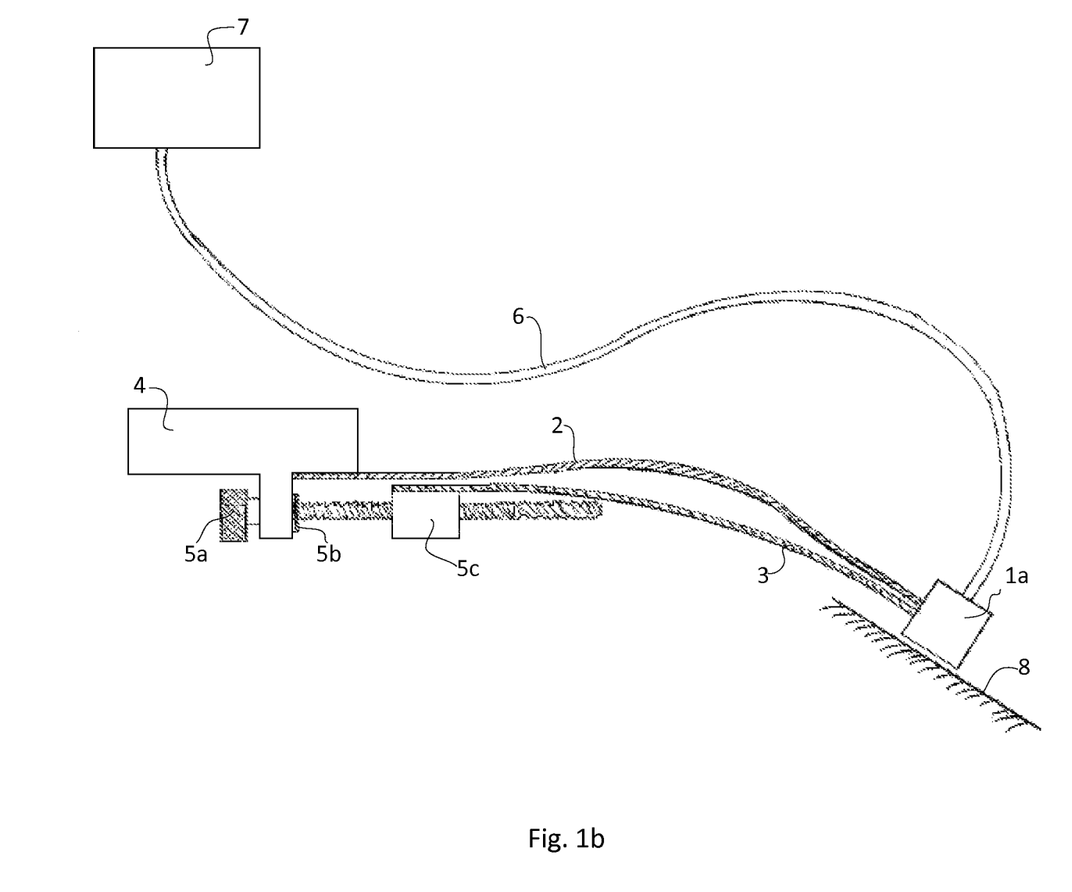
FIG. 1b is a view of the probe holder assembly shown in FIG. 1 with the adjustment arm retracted and curved in an arc shape in a second direction.

Referring to FIGS. 1a and 1b, the bending moment deflects a-type probe 1a in an adjustable arc in the thickness-length plane of adjusting arm 3, in the direction of the arm under tension. Reversing the direction of forces applied to adjusting arm 3 reverses the curvature of the arms. After a-type probe 1a is fully angled, lengthwise displacement of the arms stops; the forces couple at the arm ends in opposition through the sensor, resulting in a bending moment and arm curvature.

Examples of moving and holding adjusting arm 3 include, but are not limited to: a sliding motion and pinching between the index finger and thumb; a thumb actuated sliding motion and a clamp; a ratchet and pawl; a thumb-actuated drive screw; and a motor driven screw. It should be recognized by those skilled in the art that other means for adjusting and holding the arms to apply and hold a force used to adjust the curvature of the probe holder assembly are within the scope of the present disclosure.

Figure 2:
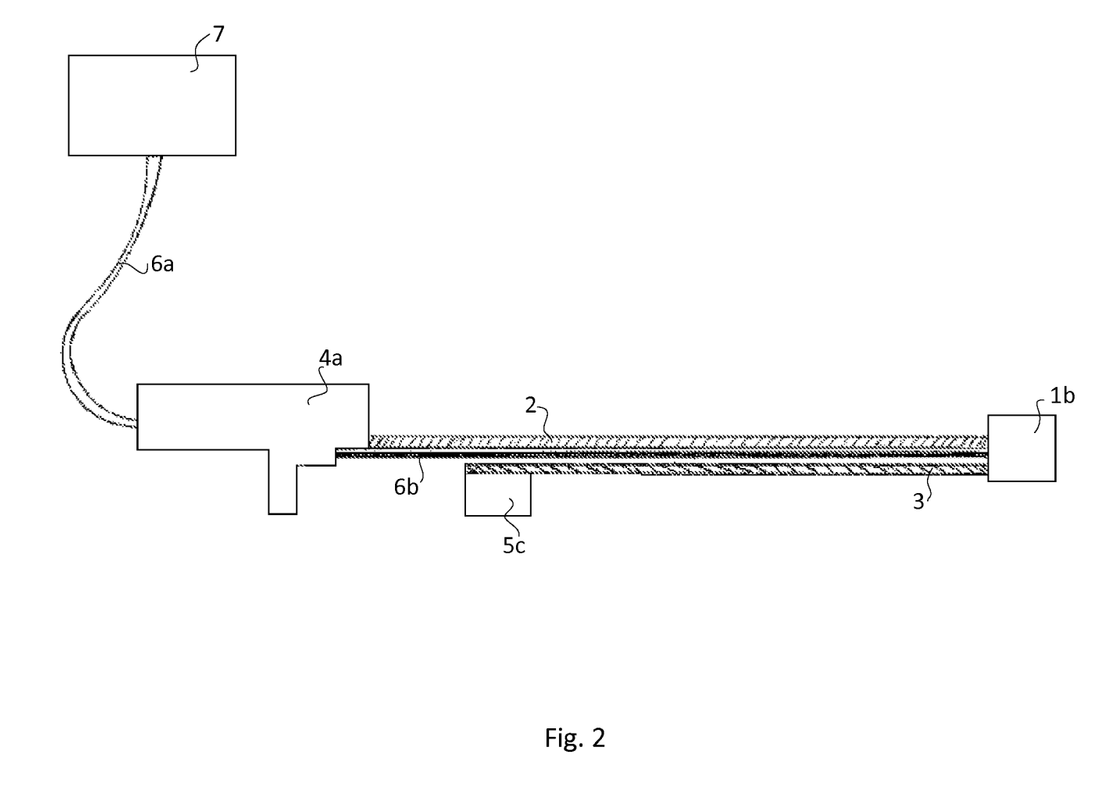
FIG. 2 is a profile view of an embodiment of the probe holder assembly, with an electrical connection.

Referring to FIG. 2, an alternative embodiment of the present disclosure is shown to differ to that of FIG. 2 with a probe cable 6b being lined sandwiched between two arms 2 and 3. This alternative embodiment is comprised of a b-type probe 1b, fixed arm 2, adjusting arm 3, a cabled handle 4a, adjusting actuator 5c, an instrument cable 6a, probe cable 6b, and measuring instrument 7.

Partially contained within cabled handle 4a, instrument cable 6a is connected to measuring instrument 7 and probe cable 6b. Adjusting actuator 5c is connected to adjusting arm 3, which is connected to b-type probe 1b. When the position of adjusting actuator 5c is moved, adjusting arm 3 bends, which subsequently adjusts the tilt of b-type probe 1b and keeps the positions of fixed arm 2 and probe cable 6b in place.

Probe cable 6b as a connecting means may include, but is not limited to, forms of the following: wires, cables, circuit boards, connectors, contact points, and conductive housings. The connecting means can be external to the probe holder assembly, between the arms, or part of the arm structure, any variation of which is within the scope of the present disclosure.

Figure 3:
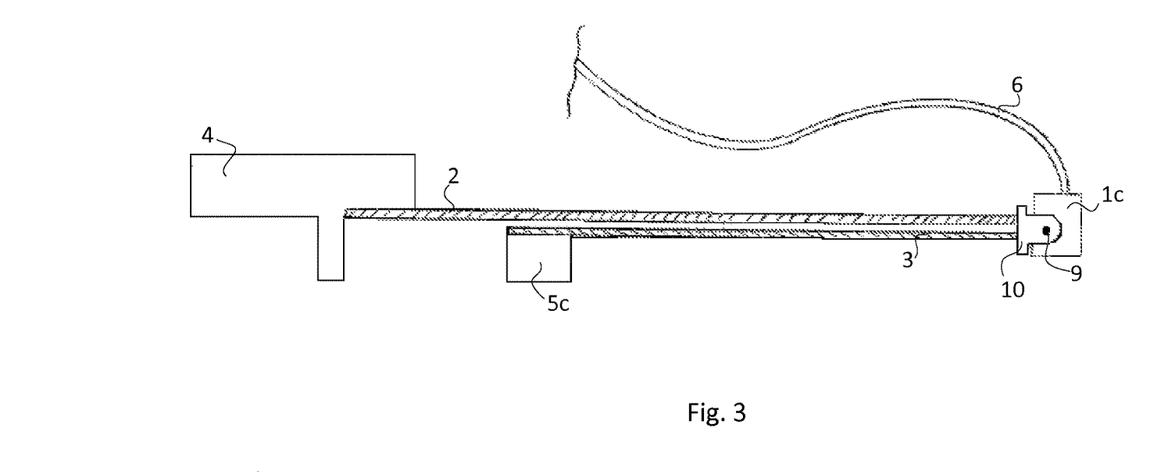
FIG. 3 is a profile view of an embodiment of the probe holder assembly having the probe holder adjustably attached to a probe housing a sensor, with a cable to a measuring instrument.

Referring to FIG. 3, a probe housing a sensor with cable can be adjustable and/or re-attachable instead of being incorporated into the probe holder assembly as in FIGS. 1 and 2. The means of attachment of the attachable probe to the arms include a coupling 10 and a joint 9. This alternative embodiment of the probe holder assembly is comprised of a (re-attachable) c-type probe 1c with coupling 10, fixed arm 2, adjusting arm 3, handle 4, adjusting actuator 5c, direct cable 6, and joint 9.

Direct cable 6 is connected to a measuring device (not shown), and to c-type probe 1c. C-type probe 1c is connected to and detachable from joint 9. Contained within handle 4, fixed arm 2 is connected to coupling 10. Coupling 10 is also connected to adjusting arm 3, and to adjusting actuator 5c. Coupling 10 is further connected to c-type probe 1c via joint 9. When the position of adjusting actuator 5c is moved, adjusting arm 3 bends, adjusting the tilt of coupling 10, joint 9, and c-type probe 1c.

Figure 3A:
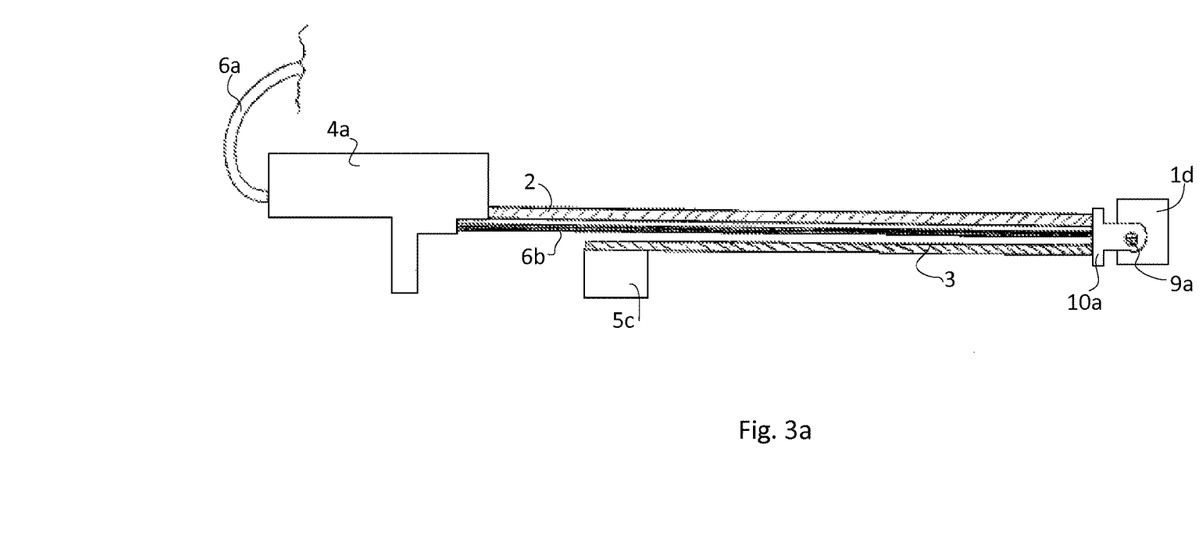
FIG. 3a is a profile view of an embodiment of the probe holder assembly having a probe adjustably attached to the probe holder and the probe having an electrical connection to the measuring instrument.

Referring to FIG. 3a, another alternative embodiment of the present disclosure is shown to embody an inter-arm electrical connection design and a re-attachable probe. The probe holder assembly in this embodiment is comprised of: a d-type probe 1d, fixed arm 2, adjusting arm 3, cabled handle 4a, adjusting actuator 5c, probe cable 6b sandwiched between arms 2 and 3, a cable-hosting coupling 10a, and a cable joint 9a.

Instrument cable 6a is connected to the instrument (not shown) via a cable holder inside cabled handle 4a. D-type probe 1d includes a sensor with electrical connection and is connected to and detachable from cable joint 9a. Contained within cabled handle 4a and fixed arm 2, probe cable 6b are connected to cable-hosting coupling 10a. Cable-hosting coupling 10a is also connected to adjusting arm 3, which is connected to adjusting actuator 5c. Cable-hosting coupling 10a is further connected to d-type probe 1d via cable joint 9a. When the position of adjusting actuator 5c is moved, adjusting arm 3 bends, which subsequently adjusts the tilt of adjusting arm 3, cable joint 9a, and d-type probe 1d.

Figure 3B:
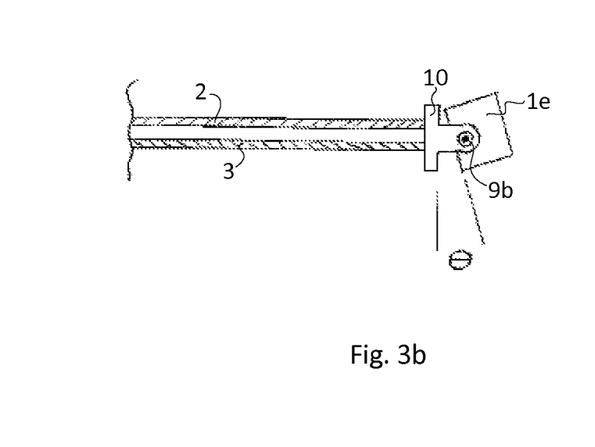
FIG. 3b is a partial profile view of an embodiment of the probe holder assembly with a probe coupling, having a pivot to allow attachment at a fixed or varying angle to a re-attachable probe housing a sensor, and with the arms adjusted to straight position.

Referring to FIG. 3b, a pivoting joint 9b alternative to cable joint 9a in FIG. 3a is used. Fixed arm 2 and adjusting arm 3 are connected to coupling 10, which is connected to an e-type probe 1e via pivoting joint 9b. E-type probe 1e tilts at an angle θ of coupling 10.

Figure 3C:
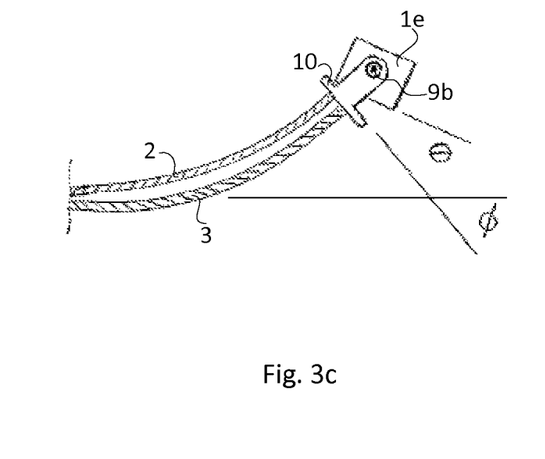
FIG. 3c is a partial profile view of the probe holder assembly shown in FIG. 3b with the adjustable arm extended and curved in an arc.

Referring to FIG. 3c, embodiment of the probe holder assembly in FIG. 3b is shown with the arms curved in an arc. E-type probe 1e tilts at angle θ of coupling 10, and also at an additional angle π/2-φ from the bend of adjusting arm 3. Fixed arm 2 stays in place relative to adjusting arm 3 when the position of adjusting arm 3 is adjusted.

Figure 4:
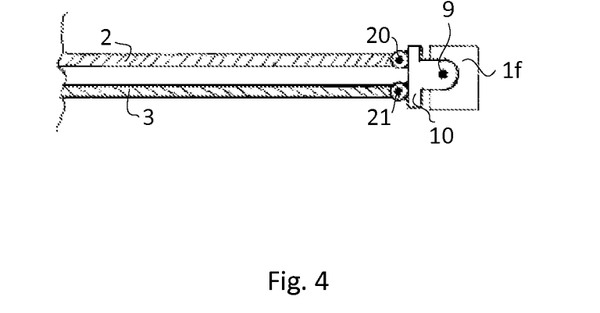
FIG. 4 is a partial profile view of an embodiment of the probe holder assembly having pivot links between the arms and a freely pivoting probe coupling with a re-attachable probe housing a sensor, and with the arms adjusted to the straight position.
Figure 4A:
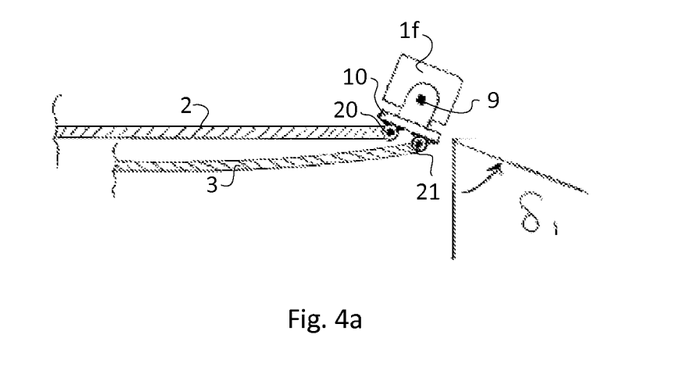
FIG. 4a is a view of the probe holder assembly shown in FIG. 4 with an adjustable arm extended to pivot the probe coupling.
Figure 4B:
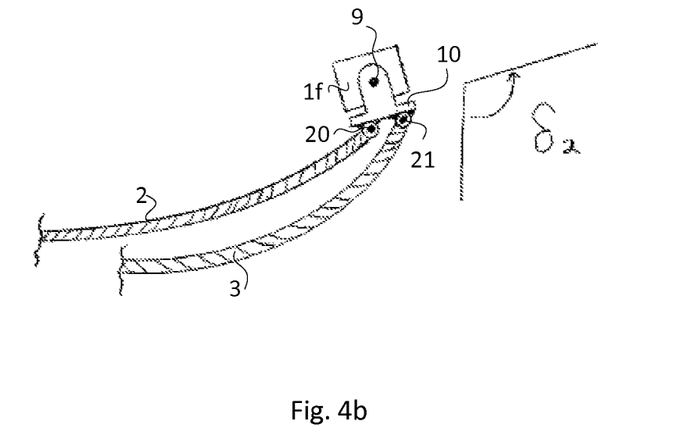
FIG. 4b is a view of the probe holder assembly shown in FIG. 4a with the adjustable arm further extended to curve the arms in an arc and to pivot the probe coupling in the same direction.

Referring now to FIGS. 4, 4a and 4b, more alternative embodiments of the disclosure having pivot links between a probe coupling and arms are shown. More specifically, in FIG. 4, a first pivot link 20 and a second pivot link 21 are shown to connect coupling 10 with fixed arm 2 and adjusting arm 3, respectively. In FIG. 4a, the combined motions are shown for adjustable arm 3, joint 9, and coupling 10. An f-type probe 1f, connected via joint 9 to coupling 10, moves at an angle δ1 when the position of adjusting arm 3 is partially extended. Referring to FIG. 4b, the combined motions in FIG. 4a can be further extended. The position of f-type probe if tilts at an angle δ2 by further extension of adjusting arm 3.

Figure 5:
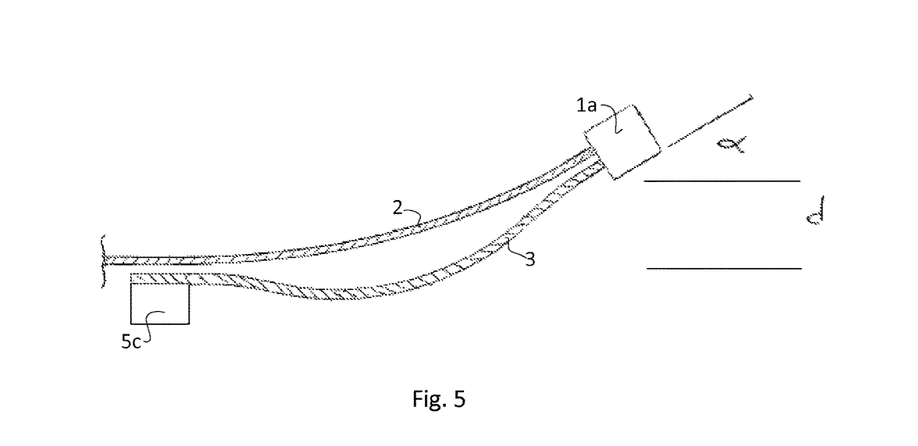
FIG. 5 is a partial profile view of an embodiment of the probe holder assembly showing mid-arm separation with a probe housing a sensor at displacement d and angle $\alpha$.

Referring to FIG. 5, in yet another group of alternative embodiments, one can achieve separation and moves of the arms of the probe holder assembly by using arm collars. The collars can be long or short, rigid or elastic, nearer the center or nearer the ends of the arms, in order to allow more or less separation between the arms to achieve a desired curve shape. A-type probe 1a tilts at a displacement d at an angle α when adjusting arm 3 bends from the movement of adjusting actuator 5c.

Figure 5A:
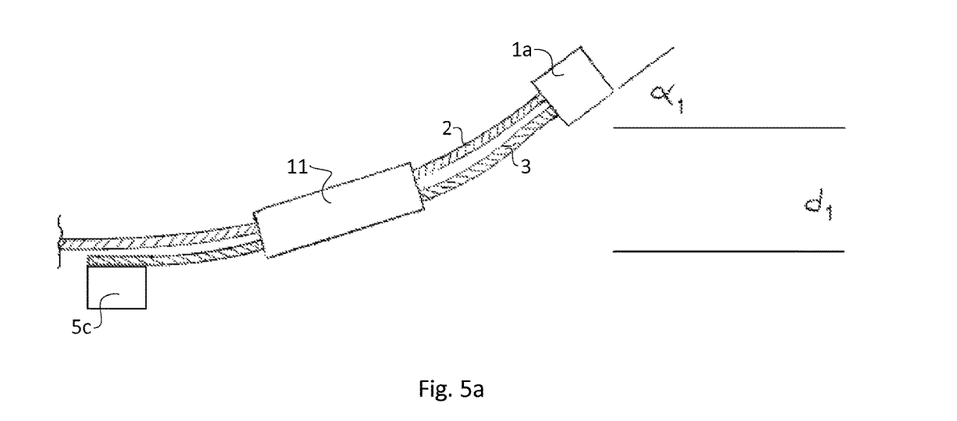
FIG. 5a is a partial profile view of an embodiment of the probe holder assembly showing mid-arm separation with a collar restricting the mid-arm separation to adjust a probe housing a sensor at displacement $d_1$ and angle $\alpha_1$.

Referring to FIG. 5a, an alternative embodiment having a collar that restricts mid-arm separation, is comprised of: a-type probe 1a, fixed arm 2, adjusting arm 3, adjusting actuator 5c, and a collar 11. Fixed arm 2 and adjusting arm 3 are connected to a-type probe 1a, and pass through collar 11. Adjusting arm 3 is connected to adjusting actuator 5c. When the position of adjusting actuator 5c is moved, adjusting arm 3 bends and a-type probe 1a tilts at a displacement $d_1$ at an angle $\alpha_1$. Displacement $d_1$ and angle $\alpha_1$ are determined by the adjustment of adjusting actuator 5c, the dimensions and elastic properties of fixed arm 2 and adjusting arm 3 and the dimensions, and the elastic properties and position of collar 11.

Figure 5B:
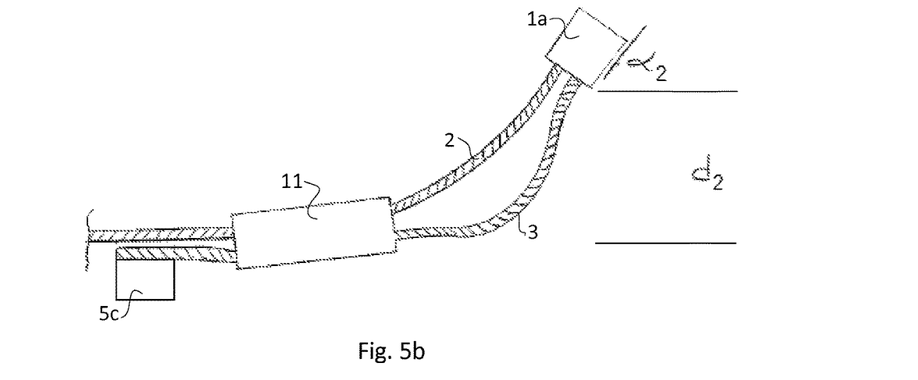
FIG. 5b is a partial profile view of an embodiment of the probe holder assembly shown in FIG. 5a with a collar restricting the arm separation near the arms end to adjust a probe housing a sensor at displacement $d_2$ and angle $\alpha_2$.

Referring to FIG. 5b, with collar 11 moved to a position at the ends of the arms, when adjusting actuator 5c is moved, adjusting arm 3 bends via collar 11, and a-type probe 1a tilts at a displacement $d_2$ at an angle $\alpha_2$.

Figure 5C:
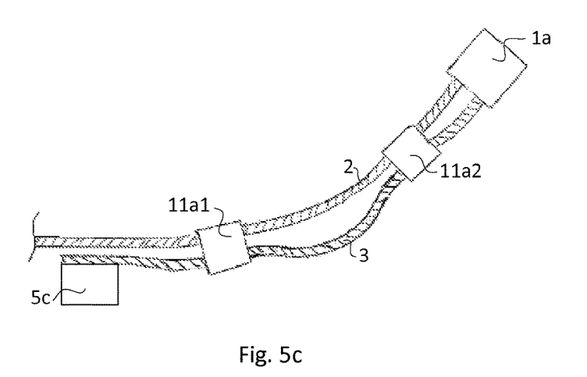
FIG. 5c is a partial profile view of an embodiment of the probe holder assembly showing mid-arm separation with multiple collars to restrict the arm separation.

Referring to FIG. 5c, an embodiment having more than one collar restricting arm separation includes a multiple collar 11a1 and a multiple collar 11a2. Fixed arm 2 and adjusting arm 3 are connected to a-type probe 1a via multiple collars 11a1 and 11a2. Adjusting arm 3 is also connected to adjusting actuator 5c through multiple collars 11a2. When the position of adjusting actuator 5c is moved, adjusting arm 3 bends via multiple collars 11a1 and 11a2, and a-type probe 1a tilts.

Figure 5D:
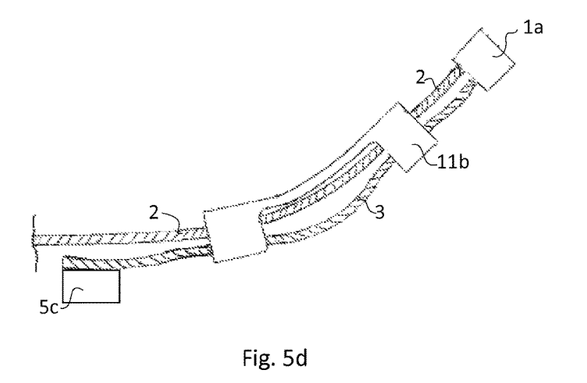
FIG. 5d is a partial profile view of an embodiment of the probe holder assembly showing mid-arm separation with a joined collar to restrict the arm separation.

Referring to FIG. 5d, yet another alternative embodiment includes a joined collar 11b. Fixed arm 2 and adjusting arm 3 are connected to a-type probe 1a via joined collar 11b. Adjusting arm 3 is also connected to adjusting actuator 5c via joined collar 11b. When the position of adjusting actuator 5c is moved, adjusting arm 3 bends via joined collar 11b, which adjusts the tilt of a-type probe 1a.

Figure 5E:
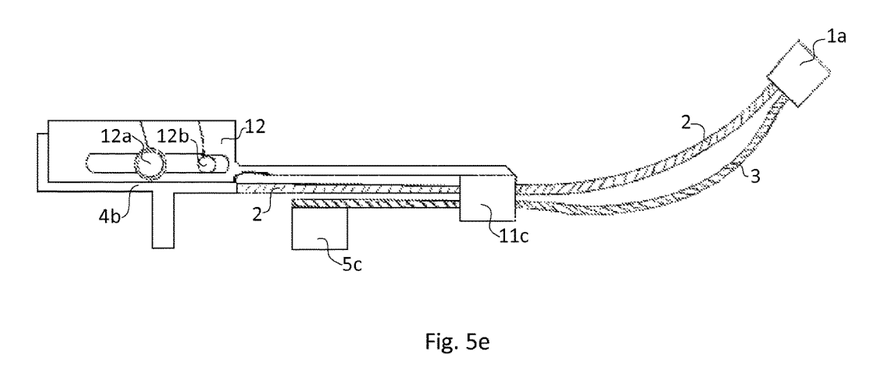
FIG. 5e is a partial profile view of an embodiment of the probe holder assembly showing mid-arm separation with a movable sleeve to restrict the arm separation.

Further referring to FIG. 5e, yet another alternative usage of a collar is shown as an embodiment with a movable sleeve 11c to restrict mid-arm separation. Movable sleeve 11c, a movable sleeve adjusting handle 12, a movable sleeve adjusting knob 12a and a movable sleeve adjusting knob guide 12b are used to control the move of adjusting arm 3. Fixed arm 2 is also connected via movable sleeve 11c to movable sleeve handle 4b. Adjusting arm 3 is connected via movable sleeve 11c to adjusting actuator 5c. Contained within movable sleeve handle 4b, movable sleeve adjusting handle 12 has movable sleeve adjusting knob 12a that a user guides through movable sleeve adjusting knob guide 12b to adjust movable sleeve 11c. When the position of adjusting actuator 5c is adjusted via movable sleeve 11c, adjusting arm 3 bends, adjusting the tilt of a-type probe 1a.

Figure 6:
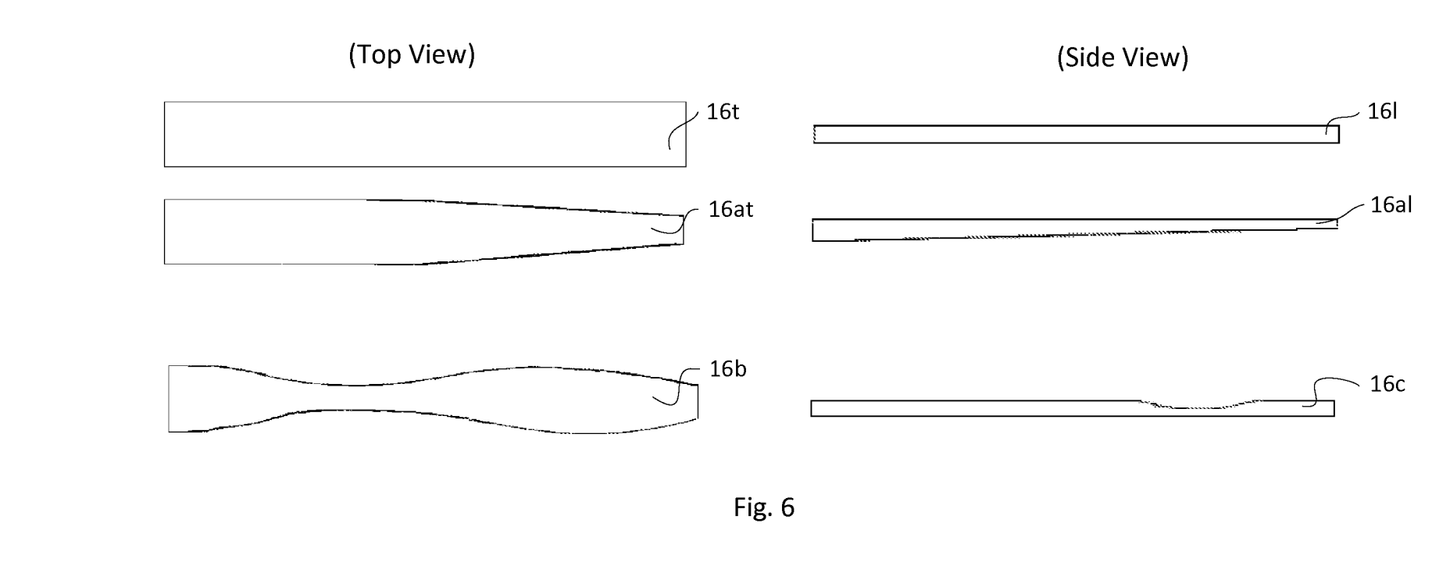
FIG. 6 shows exemplary arm width profiles of the probe holder assembly arms orthogonal to the bending plane in the top view and in the side view.
Figure 7:
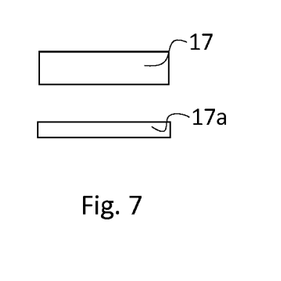
FIG. 7 shows exemplary arm thickness cross sections of the probe holder assembly arms in the thickness-width plane.

Referring to FIG. 6, the probe holder assembly arms in accordance with the present disclosure are strip shaped, the lengths and widths of each strip being greater than the thicknesses. The widths of the arms of the present disclosure (from a top view) can be in the shape of a rectangular adjusting arm 16t, a tapered adjusting arm 16at, or a narrow-waist adjusting arm 16b. From a side view, the arms can have the thicknesses of a rectangular adjusting arm 16l, a tapered adjusting arm 16al, or a hollow point adjusting arm 16c. Referring to FIG. 7 from a side width view, the arm thicknesses can be a thick width arm 17 or a thin width arm 17a. It should be appreciated that all variations of the arm shapes of the probe holder assembly are within the scope of the present disclosure.

The size and shape of the arms are determined by the limits of an application for crevice size, angle of curvature, and actuating force. A stiff arm design may support a larger probe, and allow greater holding force against the inspection surface, but requires greater actuating force to affect a bend. The stiffness of an arm is determined by its second moment of area and by its modulus. The stiffness of an arm increases with its increasing moment of area and modulus of material used in its manufacture. The arm moment is frequently determined by application requirements, and arm stiffness is determined by material selection.

Arm materials are selected for intrinsic mechanical properties such as modulus, as well as price, fabrication and aesthetic attributes. Examples of arm materials include, but are not limited to, high carbon steel, tempered stainless steel, beryllium-copper, rigid PVC, epoxy reinforced with graphite, glass or aramid fibers and bamboo.

Figure 8:
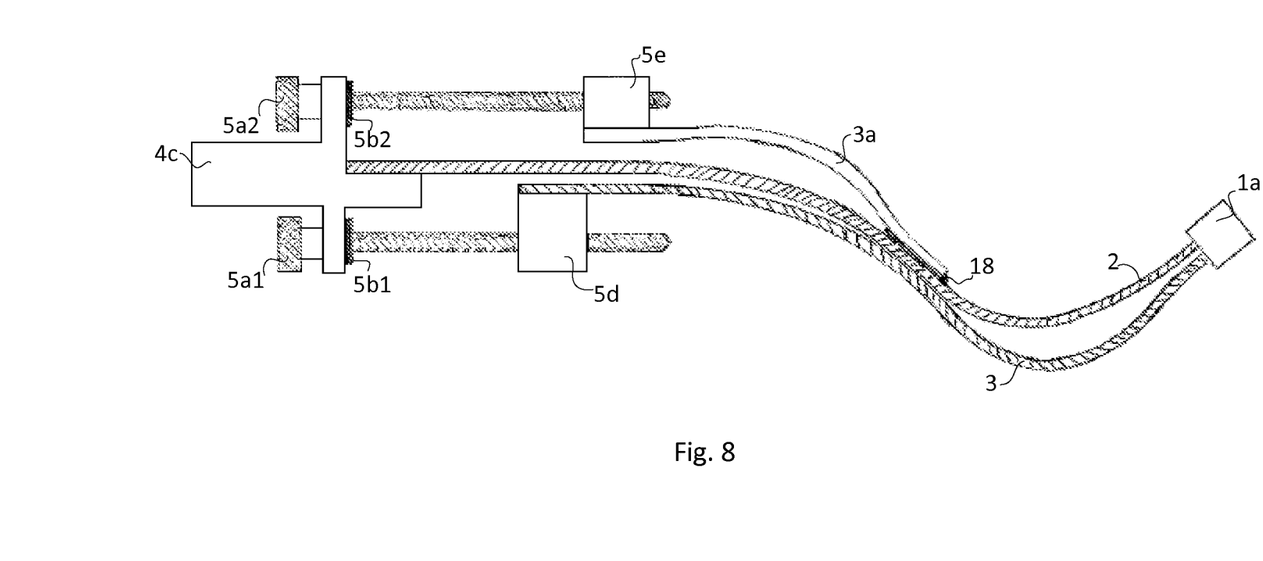
FIG. 8 is a profile view of an embodiment of the probe holder assembly with multiple adjusting arms affecting the tilt of a probe housing a sensor.

Referring to FIG. 8, further alternatively, two or more arms can be employed to cause a bending moment to occur in the probe holder assembly. Specially devised for this embodiment with multiple adjusting arms are adjusting arm 3, a second adjusting arm 3a, a multiple arm handle 4c, a first adjusting actuator screw 5a1, a second adjusting actuator screw 5a2, a first adjusting actuator retainer 5b1, a second adjusting actuator retainer 5b2, a first adjusting actuator 5d, a second adjusting actuator 5e, and an arm attachment 18.

Still referring to FIG. 8, fixed arm 2 and adjusting arm 3 are connected to a-type probe 1a. Fixed arm 2 is also coupled to second adjusting arm 3a by means of arm attachment 18, and to multiple arm handle 4c. Second adjusting arm 3a is connected to second adjusting actuator 5e. Adjusting arm 3 is also connected to first adjusting actuator 5d. Contained within multiple arm handle 4c, first adjusting actuator screw 5a1 is connected to first adjusting actuator retainer 5b1, and second adjusting actuator screw 5a2 is connected to second adjusting actuator retainer 5b2, which are connected to move first adjusting actuator 5d and second adjusting actuator 5e respectively.

When first adjusting actuator screw 5a1 is turned clockwise or counterclockwise, it results in the extension or retraction of first adjusting actuator 5d. When second adjusting actuator screw 5a2 is turned clockwise or counterclockwise, it results in the extension or retraction of second adjusting actuator 5e. When the position of first adjusting actuator 5d is moved, adjusting arm 3 bends, adjusting the tilt of a-type probe 1a. When the position of second adjusting actuator 5e is moved, second adjusting arm 3a bends, which adjusts the position of arm attachment 18, and causes fixed arm 2 to bend, also adjusting the tilt of a-type probe 1a.

Figure 9:
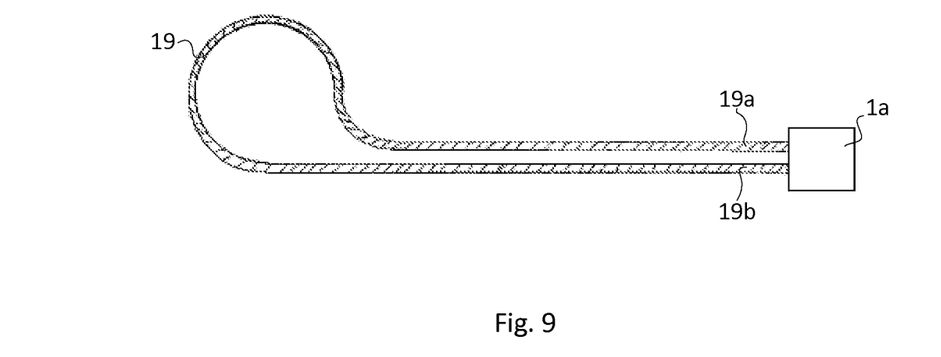
FIG. 9 is a profile view of an embodiment of the probe holder assembly having a probe housing a sensor that is attached to a pair of arms extending from a loop formed in a single strip between the arm ends.

Referring to FIG. 9, a pair of arms can be separate strips joined to other members of the probe holder assembly, or can be opposite ends of a single strip extending from a loop formed in the strip between the arm ends, the variations of which are within the scope of the present disclosure. An alternative embodiment can be comprised of a-type probe 1a attached to a first loop arm 19a and a second loop arm 19b to form an adjustable arm loop 19.

Adjustable arm loop 19 is connected to a-type probe 1a via first loop arm 19a and second loop arm 19b. The user can adjust the tilt of a-type probe 1a by pressing and rubbing together loop arms 19a and 19b.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A probe holder for holding and positioning a probe, the probe is used by an operator to conduct non-destructive testing or inspection (NDT/NDI) on a test object while being placed against a test surface of the test object, the probe holder is comprised of,
   at least two elongated holding arms, among which a first arm and a second arm, each having a probe end and a holding end,
   wherein the probe end of each of the holding arms are attached to the probe and the at least two arms remain substantially parallel along their entire length when the probe holder is at a non-operational status, and wherein the at least two arms experience a bulging open away from each other due to either a tension force or a compression force being exerted along the longitudinal direction of either one of the arms, wherein tension force in the first arm causes deflection of the probe in a first direction and compression force in the first arm causes deflection of the probe in a second direction, and wherein the bulging open causes a bending moment and a deflection of the probe towards the test surface, thereby holding the probe to be against the test surface of the test object.

2. The probe holder of claim 1 is configured to assist the operator to hold the probe to reach the test surface through a tight space having an arc-shaped path between the probe and the hand of the operator.

3. The probe holder of claim 2 wherein the two arms are connected at the holding ends and form a continuous arm.

4. The probe holder of claim 1 further comprising a handle configured to facilitate holding and adjusting the probe holder.

5. The probe holder of claim 4, wherein the holding ends of the at least two arms are attached to the handle with the holding end of the first arm secured on the handle and the holding end of the second arm adjustably attached to the handle via an adjuster.

6. The probe holder of claim 5, wherein the adjuster is configured to move the holding end of the second arm closer or further from the probe along the longitudinal direction.

7. The probe holder of claim 6, wherein the adjuster is movable by a thumb or other fingers of the operator.

8. The probe holder of claim 6, wherein the adjuster is adjustable by a screw, the screw having a screw head holed through the handle, and a screw tip portion coupled with the adjuster machined as a nut of the screw.

9. The probe holder of claim 4 further comprises a cable providing electrical connection between the probe and an NDT/NDI instrument.

10. The probe holder of claim 9, wherein the cable is connected to the probe at a different location from where the arms are attached to the probe.

11. The probe holder of claim 9, wherein the cable is connected to the probe at a close proximity from where the arms are attached to the probe.

12. The probe holder of claim 11, wherein the cable is sandwiched between the two arms and runs through the handle before connecting to the instrument.

13. The probe holder of claim 4 further comprising at least one collar placed at least one predetermined collar section of the arms and configured to loop the arms together while allowing longitudinal relative movement of the two arms.

14. The probe holder of claim 13 wherein the at least one collar is adjustably fixed onto the handle.

15. The probe holder of claim 13 wherein the at least one collar includes two collars with fixed longitudinal distance from each other.

16. The probe holder of claim 1, wherein the two arms' cross-section perpendicular to the longitudinal direction is configured to be in thin flat shapes.

17. The probe holder of claim 1, wherein the probe ends of the two arms are fixed onto the probe.

18. The probe holder of claim 1, wherein the two arms are connected to the probe via a coupling piece.

19. The probe holder of claim 18, wherein the coupling piece is configured to allow pivotal moves between the probe and the coupling piece.

20. The probe holder of claim 18, wherein the two arms are securely fixed onto the coupling piece.

21. The probe holder of claim 18, wherein the two arms are attached to pivot links pivotally attached to the coupling piece.

22. The probe holder of claim 1, wherein the two arms are of metal material.

23. The probe holder of claim 1, wherein the two arms are of plastic material.

* * * * *